United States Patent
Gantner et al.

(10) Patent No.: US 6,512,072 B1
(45) Date of Patent: Jan. 28, 2003

(54) FAST CURE FILM FORMING FORMULATION

(75) Inventors: David Clayton Gantner, Midland, MI (US); Keith Alan LaChance, Midland, MI (US); Bartley Dean Maxon, St. Louis, MI (US); Katherine Lynn Ulman, Sandford, MI (US); Debra Jo Nagy Zellner, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/591,847

(22) Filed: Jun. 12, 2000

(51) Int. Cl.$^7$ ............................................... C08G 77/18
(52) U.S. Cl. ...................... 528/34; 528/35; 523/118; 524/731; 524/588; 524/268; 106/287.14; 106/287.16; 106/15.05; 424/65; 424/59; 424/280.1; 514/772.3
(58) Field of Search ............... 528/35, 34; 523/118; 524/588, 268, 731; 106/287.14, 287.16, 15.05; 8/94.1 R; 424/65, 59, 280.1; 514/772.3

(56) References Cited

U.S. PATENT DOCUMENTS

| | | | | |
|---|---|---|---|---|
| 3,175,993 A | | 3/1965 | Weyenberg | 260/46.5 |
| 3,372,484 A | | 3/1968 | Mumaw | 32/14 |
| 3,655,865 A | | 4/1972 | Murphy | 424/45 |
| 3,708,324 A | | 1/1973 | Stebleton | 117/47 R |
| 3,836,647 A | | 9/1974 | Lange | 424/184 |
| 4,525,566 A | | 6/1985 | Homan et al. | 528/17 |
| 4,579,964 A | * | 4/1986 | Totten et al. | 556/434 |
| 4,772,675 A | | 9/1988 | Klosowski et al. | 528/17 |
| 4,871,827 A | | 10/1989 | Klosowski et al. | 528/17 |
| 4,888,380 A | | 12/1989 | Kamis et al. | 524/588 |
| 4,898,910 A | | 2/1990 | Kamis et al. | 524/860 |
| 4,906,719 A | | 3/1990 | Chu et al. | 528/17 |
| 4,962,174 A | | 10/1990 | Bilgrien et al. | 528/15 |
| 5,045,310 A | | 9/1991 | Halloran et al. | 424/71 |
| 5,209,924 A | | 5/1993 | Garbe et al. | 424/71 |
| 5,279,818 A | | 1/1994 | Halloran et al. | 424/71 |
| 5,403,881 A | | 4/1995 | Okawa et al. | 524/261 |
| 5,470,923 A | * | 11/1995 | Krahnke et al. | 525/477 |
| 5,508,360 A | * | 4/1996 | Cifuentes et al. | 525/477 |
| 6,008,284 A | | 12/1999 | Nylund et al. | 524/425 |

FOREIGN PATENT DOCUMENTS

| | | | |
|---|---|---|---|
| AU | A 17675/95 | 11/1995 | A61K/9/70 |
| DE | 3150631 A1 | 7/1983 | A01N/25/08 |
| EP | 1185943 | 3/1970 | C08G/47/02 |
| EP | 1492581 | 11/1977 | A61L/15/01 |
| EP | 0113992 A1 | 7/1984 | C08L/83/08 |
| EP | 0281204 A2 | 9/1988 | A61K/9/50 |
| EP | 0381445 A2 | 8/1990 | A61K/6/00 |
| EP | 0390541 A2 | 10/1990 | A61K/9/20 |
| EP | 0409550 A1 | 1/1991 | A61L/25/00 |
| EP | 0465744 A1 | 1/1992 | A61K/9/20 |
| EP | 0521455 A2 | 1/1993 | A61K/9/12 |
| EP | 0560014 A1 | 9/1993 | A61L/25/00 |
| EP | 0679392 A1 | 11/1995 | A61K/9/70 |
| EP | 0723341 A1 | 7/1996 | H03M/7/30 |
| EP | 0747443 A2 | 12/1996 | C08L/83/04 |
| EP | 0865787 A1 | 9/1998 | A61K/9/70 |
| IT | 1214978 | 1/1990 | A61F/000/00 |
| JP | 6319464 | 11/1994 | A23K/1/10 |
| WO | WO 90/03809 | 4/1990 | A61L/15/00 |
| WO | WO 97/15295 | 5/1997 | A61K/9/70 |

OTHER PUBLICATIONS

Kirk–Othmer Encyclopedia "Silicon Compounds (Silicones)". vol. 20, p. 942. 1982.*

* cited by examiner

*Primary Examiner*—Margaret G. Moore
(74) *Attorney, Agent, or Firm*—Charles R. Richard; Roger E. Gobrogge

(57) ABSTRACT

A formulation for depositing a film on a substrate comprising 5 to79.9 wt. % of an alkylene trialkoxy terminated polysiloxane; 0.01 to 5 wt. % of a catalyst; 20 to 94.99 to wt % of a volatile diluent, and, optionally, 0.01 to 5 wt. % of an alkoxysilane and 0.1 to 25 wt % of a filler. The formulations are especially valuable for forming films to be used in personal care or healthcare applications.

9 Claims, No Drawings

FAST CURE FILM FORMING FORMULATION

BACKGROUND OF THE INVENTION

The present invention relates to one-part formulations which rapidly cure on exposure to moisture and are useful for forming films in personal and healthcare applications. The formulations comprise an alkylene trialkoxy terminated siloxane; a catalyst; a diluent; and, optionally, an alkoxysilane and/or a filler.

Many formulations for forming films are known in the pharmaceutical art. These include, for example, ointments, salves, creams, lotions, gels, elastomers and the like. Some of these formulations use silicone-based materials as key components. Silicone based materials are desirable in these formulations since they are generally inert to the body.

One example of silicon-based materials in film forming formulations is provided in European publication number 465,744. This publication teaches the use of a multi-part formulation including an active agent, a Si-H containing polymer, a polymer having unsaturated groups bound to silicon, a catalyst and a hydrophilic component. This formulation is mixed and applied to the body where it cures and forms a controlled release gel.

The prior art methods such as those described in EP 465,744, however, have several disadvantages. For instance, in such methods the person utilizing the formulation must be skilled so as to ensure adequate mixing of the appropriate amounts of component materials in the formulation and then applying the correct amount of the mixed formulation to the desired site before it gels. Similarly, such a method can be an inconvenience and messy for the user. Finally, these methods involve ingredients that may not be desirable for healthcare applications.

WO 90/03809 teaches a coating material for forming bandages comprising a siloxane containing bandage material diluted in a volatile polydimethylsiloxane. The materials described in this reference, however, are different than those described and claimed herein.

Finally, patent such as U.S. Pat. Nos. 3,175,993, 4,772,675, 4,871,827, 4,888,380, 4,898,910, and 4,906,719 teach silicone sealants comprising an alkylene trialkoxysilyl terminated polysiloxane; an alkoxysilane; and a catalyst. Such references, however, do not teach the compositions or the uses described and claimed herein.

We have now discovered a formulation for making a film which can avoid many of the above prior art problems.

SUMMARY OF THE INVENTION

The present invention relates to a formulation comprising 5 to 79.99 wt. % of an alkylene trialkoxysilyl terminated polysiloxane; 0 to 5 wt. % of an alkoxysilane; 0.01 to 5 wt. % of a catalyst; 0 to 25 wt % of a filler; and 20 to 94.99 wt % of a volatile diluent.

The present invention also relates to a method for forming a film on a substrate comprising mixing the above components and applying the formulation onto the desired site, wherein said formulation cures in situ on the desired site to form the film.

DETAILED DESCRIPTION OF THE INVENTION

The present invention relates to formulations which are useful for forming films on substrates, preferably biological substrates, where they can serve, for example, as barrier films, cosmetic films, drug delivery mechanisms and the like.

The first component in the formulations of the present invention comprises alkylene alkoxy terminated polysiloxanes. The polymers may be linear or branched and may be homopolymers, copolymers, or terpolymers. Moreover, the polymers may be a single species or a mixture of different polymers. Typically, it is preferred that these polymers have, on average, at least 1.2 alkylene trialkoxysilyl chain terminations per molecule.

The monomeric units of these polymers may include organic units, such as ethylene, butylene, or oxyalkylene units, but preferably a majority of the monomeric units are siloxy units such as those described by the formula $R^9_s SiO_{(4-s)/2}$, where each $R^9$ is independently selected from the group consisting of alkyl groups comprising 1 to about 6 carbon atoms, phenyl, and fluorinated alkyl groups, and s is 0, 1, 2 or 3. Examples of the alkyl groups described by $R^9$ include methyl, ethyl, propyl, butyl and hexyl. An example of the fluorinated alkyl groups described by $R^9$ includes 3,3,3-trifluoropropyl. The preferred polymers comprise polydiorganosiloxanes having repeating units described by the formula $—(R^9_2 SiO_2)_f—$, wherein each $R^9$ is as described above, preferably methyl, and f is a value such that the polymer has a viscosity within a range of about 0.5 to 3000 Pa·s at 25° C. and preferably within a range of about 5 to 150 Pa·s at 25° C.

These polymers preferably comprise, on average, at least 1.2 alkylene trialkoxysilyl chain terminations per molecule described by formula $—ZSiR^1_x(OR)_{3-x}$, wherein each R is independently selected from the group consisting of methyl, ethyl, n-propyl, isopropyl, n-butyl, sec-butyl, and isobutyl, $R^1$ is selected from the group consisting of methyl and ethyl, and x is 0 or 1. In preferred embodiments, each R is independently selected from the group consisting of methyl and ethyl, and x is zero. Z in the above formula is independently selected from the group consisting of divalent hydrocarbon radicals free of aliphatic unsaturation comprising about 2 to 18 carbon atoms and a combination of divalent hydrocarbon radicals and siloxane segments described by the formula

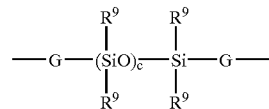

wherein $R^9$ is as defined above, each G is a divalent hydrocarbon radical free of aliphatic unsaturation comprising about 2 to 18 carbon atoms, and c is a whole number from 1 to about 6. Examples of the divalent hydrocarbon radicals describing Z and G include alkylene radicals such as ethylene, propylene, butylene, pentylene, and hexylene; and arylene radicals including phenylene. Preferably, Z is alkylene with ethylene being particularly preferred.

These polymers typically have, on average, at least 1.2 alkylene trialkoxysilyl chain terminations per molecule, and preferably, have, on average, at least 1.5 alkylene trialkoxysilyl chain terminations per molecule. Since these polymers may have on average at least 1.2 alkylene trialkoxysilyl chain terminations per molecule, some polymers may contain other types of chain terminations. Preferably, this other type of chain termination comprises organosilyl chain terminations selected from the group consisting of $CH_2=CH—SiR^9_2—$ and $R^6_3—Si—$, where $R^9$ is as defined above and each $R^6$ is independently selected from the group consisting of $R^9$ and vinyl. Examples of organosilyl chain terminations include trimethylsilyl, triethylsilyl, vinyldimethylsilyl, and vinylmethylphenylsilyl.

Polysiloxanes useful herein include those described in U.S. Pat. Nos. 3,175,993, 4,772,675, 4,871,827, 4,888,380, 4,898,910, 4,906,719, and 4,962,174, which are hereby incorporated by reference, and can be described, for example, by the formula

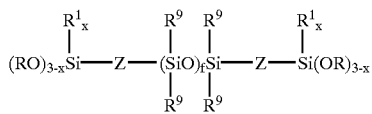
(I)

wherein R, $R^1$, $R^9$, Z, x, and f are as described above. These polymers can be made as described in the above patents.

Other polymers useful in this invention are mixtures of the polysiloxanes described by this formula (I) with trialkyl terminated siloxanes and/or the polysiloxanes described by Kamis et al., U.S. Pat. No. 4,898,910, which is hereby incorporated by reference, and described, for example, by the formula

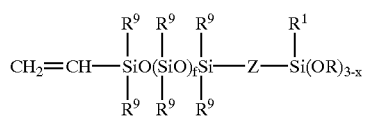
(II)

wherein R, $R^1$, $R^9$, Z, x and f are as defined above.

When the polymer comprises mixtures of polysiloxanes described by the above formulas, typically the polysiloxanes will be present in an amount such that 40 percent or less of the chain terminations will be organosilyl chain terminations, and preferably in an amount such that less than 25 percent of the chain terminations are organosilyl chain terminations.

The most preferred polymers useful in this invention are those polymers described by the polysiloxane formula (I).

The polymers useful herein can also include organic units. One type of organic polymer useful in the invention is the polyoxyalkylene, described by Okawa et al., U.S. Pat. No. 5,403,881, and hereby incorporated by reference to show polyoxyalkylene polymers comprising on average at least 1.2 alkylene trialkoxysilyl chain terminations per molecule and methods of preparing these polymers. Other organic units such as polyisobutylenes, polyethylenes, acrylics, amides and the like can also be included.

The amount of polymer useful in formulations of the present invention is dependent on the amounts of other components added but is typically in the range of about 5 to about 79.99 weight percent based on the total weight of the formulation. Preferably, the polymer is added in amounts from about 15 to 50 weight percent on the same basis.

The present formulation also includes a catalyst. Although nearly any suitable catalyst (e.g., metal containing materials) will work herein, the preferred agent is a titanium containing material. A preferred titanium material comprises a tetraalkoxytitanium compound described by average formula $Ti(OR^2)_y(OR^3)_{4-y}$, where each $R^2$ is independently selected from the group consisting of tertiary alkyl radicals and 2,4-dimethyl-3-pentyl; each $R^3$ is an independently selected alkyl radical comprising from 1 to about 6 carbon atoms; and y is an average value of from 3 to 4.

Examples of tertiary alkyl radicals represented by $R^2$ include tertiary butyl and tertiary amyl. Preferably, each $R^2$ is an independently selected tertiary alkyl radical. More preferably each $R^2$ is independently selected from the group consisting of a tertiary butyl radical and a tertiary arnyl radical.

Examples of alkyl radicals comprising from 1 to about 6 carbon atoms represented by $R^3$ include methyl, ethyl, n-propyl, isopropyl, n-butyl, sec-butyl, and hexyl.

In this formula, y is an average value of from 3 to 4. Preferably, y is an average value of from about 3.4 to 4, with an average value from about 3.6 to 4 being most preferred.

The amount of catalyst useful in the present formulations is dependent on the amounts of other components added, but is typically used in amounts in the range of about 0.01 to 5 weight percent based on the total weight of the formulation. Preferably, the catalyst is a tetraalkoxytitanium compound and it is added in amounts in the range of about 0.3 to 2.3 weight percent on the same basis. The tetraalkoxytitanium compound may be a single species or a mixture of two or more species.

The formulations of the present invention also include diluents. Such diluents are often necessary to decrease the viscosity of the formulation sufficiently for application. Examples of diluents include silicon containing diluents such as hexamethyldisiloxane, octamethyltrisiloxane, and other short chain linear siloxanes, cyclic siloxanes such as octamethylcyclotetrasiloxane and decamethylcyclopentasiloxane, dodecamethylcyclohexasiloxane, organic diluents such as alkanes, alcohols, ketones, esters, hydrofluorocarbons or any other material which can dilute the formulation without adversely affecting any of the component materials of the formulation or the curing time.

The above diluents are often used in amounts of up 94.99 wt. % of the formulation. Preferably, the diluent is used in an amount of between about 30 and 90 wt % and more preferably between about 45 and 80 wt % of the formulation. On application, however, the diluent often substantially volatilizes leaving the other component materials on the desired site.

The present formulations can also comprise an alkoxysilane described by formula $R^4{}_zSi(OR^5)_{4-z}$, where each $R^4$ is independently selected from the group consisting of alkyl radicals comprising from 1 to about 12 carbon atoms and alkenyl radicals comprising from 1 to about 12 carbon atoms; each $R^5$ is independently selected from the group consisting of methyl and ethyl, and z is 1 or 2. Preferably z is 1.

The alkyl radicals comprising 1 to about 12 carbon atoms represented by $R^4$ include, for example, methyl, ethyl, isobutyl, hexyl, octyl, and dodecyl. The alkenyl radicals comprising 1 to about 12 carbon atoms represented by $R^4$ include for example vinyl, allyl, butadienyl, and hexenyl. Preferably, each $R^4$ is independently selected from the group consisting of methyl, ethyl, isobutyl and vinyl. More preferably each $R^4$ is methyl.

Examples of useful alkoxysilanes include methyltrimethoxysilane, methyltriethoxysilane, ethyltriethoxysilane, vinyltrimethoxysilane, vinyltriethoxysilane, ethyltrimethoxysilane, octyltriethoxysilane, dimethyldimethoxysilane, vinylmethyldimethoxysilane, dimethyldiethoxysilane, isobutyltrimethoxysilane, and ethylmethyldiethoxysilane. The partial hydrolyzates of these alkoxysilanes can also be used in the present formulation. Preferred alkoxysilanes include methyltrimethoxysilane and dimethyldimethoxysilane.

If used, the amount of alkoxysilane is dependent on the amounts of other components added, but is typically in the range of 0.1 to 5 weight percent based on the total weight of the formulation, with amounts in the range of about 0.1 to 2 weight percent on the same basis being preferred. The alkoxysilane may be a single species or a mixture of two or more species.

The present formulations can also comprise fillers. The fillers can include, but are not limited to, ground, precipitated, and colloidal calcium carbonates which can be untreated or treated with stearate or stearic acid; reinforcing silicas such as fumed silicas, precipitated silicas, and hydrophobed silicas; crushed quartz, ground quartz, alumina, aluminum hydroxide, titanium dioxide, diatomaceous earth, iron oxide, carbon black, and graphite. One class of preferred fillers are synthetic silicas where the surfaces of the silica are modified with silicon compounds to produce a hydrophobic behavior. These materials differ from one another in surface area, the silicon compound used to treat the silica, and the extent of surface treatment. Such materials are surprisingly able to reduce the viscosity of the film forming formulation. In addition, resinous reinforcing fillers can be used herein to form transparent films. Silica, calcium carbonate and resinous fillers are especially preferred. Specific examples include Cab-O-Sil® TS-530 treated filler, Aerosil® R8200 treated filler, and Wacker® HDX H2000 treated filler.

If used, the amount of filler in the formulation is generally that amount which provides the desired properties to the uncured formulation such as viscosity, thixotropy, pigmentation, and UV protection. The amount of filler also depends upon the cured physical properties desired such as tensile strength, elongation, and durometer. Finally, the amount of filler also depends on the amounts of other components added, as well as the hydroxyl content of the specific filler used. Typically, this is an amount in the range of about 0.1 to 25 weight percent based on the total weight of the formulation. Preferably, the filler is added in amounts from about 2 to 15 weight percent on the same basis. The filler may be a single filler or a mixture of two or more fillers.

Other materials such as active agents can also be added to formulations of the present invention. The active agents used in the present invention are generally not critical. They can comprise any solid or liquid material which can be bound in the composition and subsequently released at the desired rate. The active agent should also not interfere with the curing of the silicone formulation to an unacceptable extent. Suitable active agents include cosmetics, therapeutic or diagnostic materials, pesticides, herbicides, and the like.

Therapeutic active agents which may be employed include, for example, antibiotic, antiseptic, antifungal, antibacterial, antiinflammatory, hormones, anticancer agents, smoking cessation compositions, cardiovascular, histamine blocker, bronchodilator, analgesic, antiarrythmic, antihistamine, alpha-1 blocker, beta blocker, ACE inhibitor, diuretic, antiaggregant, sedative, tranquillizer, anticonvulsant, anticoagulant agents, vitamins, antiaging agents, agents for treating gastric and duodenal ulcers, anticellulites, proteolytic enzymes, healing factors, cell growth nutrients, peptides and others. Specific examples of suitable therapeutic active agents include penicillins, cephalosporins, tetracyclines, macrolides, epinephrine, amphetamines, aspirin, barbiturates, catecholamines, benzodiazepine, thiopental, codeine, morphine, procaine, lidocaine, benzocaine, sulphonamides, ticonazole, perbuterol, furosamide, prazosin, prostaglandins, salbutamol, indomethicane, diclofenac, glafenine, dipyridamole, theophylline and retinol.

In addition to the therapeutic or diagnostic materials, active agents could be cosmetics such as perfumes, UV protectors, shaving products, deodorants or the like. Suitable cosmetics are known to those skilled in the art.

The proportion of the active agent employed in the present invention is chosen in accordance with the concentration of the active agent required in the composition to deliver the dosage required at the proposed delivery rate. This may vary within a wide range such as from 0.1 to about 70 weight percent, preferably 0.1 to 20 weight percent, of the final composition.

If desired the formulation may also contain other additional ingredients. One advantageous additive is a water scavenger to prevent early curing of the formulation. Other optional ingredients include colorants, coloured indicators, other diluents, extenders such as silicone fluids, silicone resins, excipients employed in pharmacy, compounds intended to perform as pH buffers in controlling the environment immediately in and around the formulation, stabilizers, preservatives, surfactants for cellular formulations such as fluorinated silicones, processing aids such as cyclic or linear polydiorganosiloxanes, bioadhesive materials, and hydrophilic, modulating and swellable components or polymers as set forth in EP Publication 465,744. Still other additional ingredients include absorbents for wounds, alginate, polysaccharides, gelatin, collagen, and materials that can decrease the friction on the surface of the cured film and/or change its gloss.

Since mixing of the component materials in the formulation causes curing at room temperature in the presence of moisture, the component materials can be mixed and stored in a moisture proof container or they can be stored in a plurality of containers prior to use to inhibit curing prior to use. Moisture proof containers include, for example, single use containers (e.g., foil packets). When using a plurality of containers, one container could, for example, contain the silane and a second could contain the polysiloxanes. Each of the additional components in the formulation is put in the container that is most desirable depending on factors such as stability, viscosity, and interactions. Often, however, it is preferable to include an active agent, if used, in only one of the parts of the formulation in order to preserve its effectiveness. Similarly, it is often desirable to put a diluent in both containers.

According to the method of the invention, the mixed formulation is applied to the desired site or, alternatively, the component materials of the invention can be applied onto the desired site in a manner that causes mixing. The formulation reacts in the presence of moisture and results in a cured composition. Preferably, the formulations are applied on a biological surface including, but not limited to animal bodies (eg., human or other animal) and flora.

The formulations of the invention can be applied, for example, by rubbing, painting, spraying, or any other conventional method of applying thin films.

As noted above, when the formulation is mixed, it cures rapidly at room temperature in the presence of moisture (e.g., within 10 minutes, usually within 1–2 minutes). For example, the formulation will cure rapidly on a human or other animal body. If used on an animal, this can minimize the amount time necessary to keep the area immobile while curing takes place.

The final composition can be in the form of a gel or an elastomer and it can have pores (e.g., foams) or it can be pore-free.

The present invention offers numerous advantages over the prior art. The method described herein allows for a simple method of forming a film on a substrate. As such, a skilled practitioner is not required for application. Moreover, the composition can be formed into a wide variety of shapes and have selected combinations of properties (e.g. bioadhesion, release rate and release profile). Similarly, the formulations and processes described herein don't involve severe conditions (e.g. high temperatures or pressures) that might damage any active agents or substrates used.

The formulations and resultant compositions herein are generally acceptable on many biological membranes. The composition may be formed on intact or damaged skin or in a natural or artificial cavity of the body. The cavity may be, for example, the ocular, buccal, nasal, aural, vaginal or rectal cavity or a cavity formed, for example, in a tooth or an open wound.

The resultant films are typically thin and non-tacky. Films on the order of up to 20 mils (e.g., 1 to 15 mils) are often obtained. These films can have many physical properties from gels to elastomers so that they are able to withstand many of the pressures exerted during normal activities of a patient.

The following non-limiting Examples are provided to assist in understanding the invention. Unless indicated, all parts are by weight and all viscosities are at 25° C.

EXAMPLES 1–2

Formulations of the present invention were made by blending the components listed in Table 1. The polymer used in these Examples was the reaction product of vinyl-terminated dimethylsiloxane with trimethoxysilylethyl tetramethyldisiloxane. The filler used in these Examples was Cab-O-Sil® TS-530 treated filler. The alkoxysilane used in these Examples was methyltrimethoxysilane. The catalyst used in these Examples was tetra-tert-butyl titanate in mixed isopropoxy and t-butoxy-titanium complexes. The diluent used in these Examples was hexamethyldisiloxane.

The materials were blended by adding, in order, the solvent, filler, polymer, silane, and catalyst to a Lightnin® rotating shaft mixer.

TABLE 2

| | | Example # | | | | | |
|---|---|---|---|---|---|---|---|
| | | 33 | 34 | 35 | 36 | 37 | 38 |
| Polymer | % | 19.19 | 23.03 | 26.87 | 30.71 | 34.55 | 19.19 |
| Filler | % | 4.8 | 5.76 | 6.72 | 7.68 | 8.64 | 4.8 |
| Alkoxy-silane | % | 0.43 | 0.52 | 0.60 | 0.69 | 0.78 | 0.43 |
| Catalyst | % | 0.58 | 0.69 | 0.81 | 0.92 | 1.04 | 0.58 |
| Diluent | % | 75.0 | 70.0 | 65.0 | 60.0 | 55.0 | 75.0 |
| | | 100 | 100 | 100 | 100 | 100 | 100 |

Samples, 0.3 grams, of the above materials were spread in a 1.5-inch diameter circle on a 3M® Scotchpak® release liner film. The materials were allowed to cure for 24 hours at room temperature. Five-micrometer measurements were taken at different locations around the liner, the readings were averaged and the release liner thickness was deducted to get the result set forth in Table 3.

TABLE 3

| Example # | % Solids | Amount | Dry Film Thickness |
|---|---|---|---|
| 33 | 25 | 0.3 | 5 Mil |
| 34 | 30 | 0.3 | 6 Mil |
| 35 | 35 | 0.3 | 7.5 Mil |
| 36 | 40 | 0.3 | 8 Mil |
| 37 | 45 | 0.3 | 10 Mil |
| 38 | 25 | 0.3 | 5 Mil |

EXAMPLES 39–47

A 32.5×32.5 cm square piece of 3M® Scotchpak® release liner film was clamped on a tabletop coater. The shims as indicated in Table 4 were clamped to the outside edges of the

TABLE 1

| | | Example # | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Polymer | % | 9.5 | 9.0 | 9.1 | 8.6 | 6.6 | 6.4 | 6.4 | 6.2 | 66.3 | 62.8 | 63.6 | 60.3 | 46.5 | 44.7 |
| Filler | % | 0.5 | 0.4 | 0.4 | 0.4 | 3.3 | 3.2 | 3.2 | 3.1 | 3.3 | 3.1 | 3.2 | 3.0 | 23.2 | 22.4 |
| Alkoxysilane | % | 0.05 | 0.04 | 0.4 | 0.4 | 0.03 | 0.03 | 0.3 | 0.3 | 0.3 | 0.3 | 3.2 | 3.0 | 0.2 | 0.2 |
| Catalyst | % | 0.01 | 0.5 | 0.01 | 0.5 | 0.01 | 0.4 | 0.01 | 0.4 | 0.07 | 3.8 | 0.07 | 3.6 | 0.05 | 2.7 |
| Diluent | % | 90 | 90 | 90 | 90 | 90 | 90 | 90 | 90 | 30 | 30 | 30 | 30 | 30 | 30 |
| | | 100 | 100 | 100 | 100 | 100 | 100 | 100 | 100 | 100 | 100 | 100 | 100 | 100 | 100 |

| | | Example # | | | | | | | | | | | | | | | | |
|---|---|---|---|---|---|---|---|---|---|---|---|---|---|---|---|---|---|---|
| | | 15 | 16 | 17 | 18 | 19 | 20 | 21 | 22 | 23 | 24 | 25 | 26 | 27 | 28 | 29 | 30 | 31 | 32 |
| Polymer | % | 45.1 | 43.5 | 16.9 | 16.5 | 16.6 | 16.2 | 15.0 | 14.6 | 14.8 | 14.4 | 46.4 | 45.3 | 45.6 | 44.5 | 41.2 | 40.3 | 40.6 | 39.7 |
| Filler | % | 22.6 | 21.7 | 2.5 | 2.5 | 2.5 | 2.4 | 4.5 | 4.4 | 4.4 | 4.3 | 7.0 | 6.8 | 6.8 | 6.7 | 12.4 | 12.1 | 12.2 | 11.9 |
| Alkoxysilane | % | 2.3 | 2.2 | 0.2 | 0.2 | 0.6 | 0.6 | 0.2 | 0.2 | 0.5 | 0.5 | 0.7 | 0.7 | 1.6 | 1.6 | 0.6 | 0.6 | 1.4 | 1.4 |
| Catalyst | % | 0.04 | 2.6 | 0.3 | 0.8 | 0.3 | 0.8 | 0.3 | 0.7 | 0.3 | 0.7 | 0.9 | 2.3 | 0.9 | 2.2 | 0.8 | 2.0 | 0.8 | 2.0 |
| Diluent | % | 30 | 30 | 80 | 80 | 80 | 80 | 80 | 80 | 80 | 80 | 45 | 45 | 45 | 45 | 45 | 45 | 45 | 45 |
| | | 100 | 100 | 100 | 100 | 100 | 100 | 100 | 100 | 100 | 100 | 100 | 100 | 100 | 100 | 100 | 100 | 100 | 100 |

EXAMPLES 33–38

Materials were made as in Examples 1–32 having the composition as set forth in the following Table 2.

release liner. A smooth surfaced coating bar was placed in position. Approximately 50 ml of the formulation was poured on the release liner in contact with the coating bar. The coater was run at medium speed to coat the release liner with the formulation. The formulation was allowed to cure for twenty-four hours at ambient temperature. Five micrometer measurements were taken at differemt locations around the circle, the readings were averaged and the release liner thickness was deducted to get the result set forth in Table 4.

TABLE 4.

| Example # | Material from Example # | % Solids | Shims | Dry Film Thickness |
|---|---|---|---|---|
| 39 | 38 | 25 | 2 mil | 1 mil |
| 40 | 38 | 25 | 5 mil | 1.5 mil |
| 41 | 33 | 25 | 30 mil | 5 mil |
| 42 | 34 | 30 | 30 mil | 6 mil |
| 43 | 35 | 35 | 30 mil | 7.5 mil |
| 44 | 36 | 40 | 30 mil | 8 mil |
| 45 | 37 | 45 | 5 mil | 3 mil |
| 46 | 37 | 45 | 30 mil | 10 mil |
| 47 | 37 | 45 | 60 mil | 17 mil |

EXAMPLES 48–50

Materials from Examples 33, 34 and 36 were cured in an 8 inch×8 inch Teflon® coated pan for 16 hours at room temperature and 4 hours at 100 C. Pieces of the cured material were die cut and their physical properties tested on an Instron Material Tester. The results are set forth in Table 5.

TABLE 5.

| Example # | 48 | 49 | 50 |
|---|---|---|---|
| Material from Example # | 33 | 34 | 36 |
| Tensile (psi) | 986 | 1070 | 1061 |
| Elongation (%) | 625 | 726 | 680 |
| 100% Modulus (psi) | 168 | 157 | 153 |
| 200% Modulus (psi) | 243 | 218 | 227 |
| 300% Modulus (psi) | 347 | 301 | 326 |
| 600% Modulus (psi) | 919 | 755 | 846 |
| Durometer (Shore A) | 46.6 | 45.9 | 43.9 |
| Tear (ppi) | 121 | 121 | 146 |

That which is claimed is:

1. A method for forming a film on a biological membrane comprising;
  mixing components comprising 5 to 70 wt. % of an alkylene trialkoxysilyl terminated polysiloxane; 0 to 5 wt. % of an alkoxysilane; 0.01 to 5 wt. % of a catalyst; 0 to 25 wt % of a filler; and 1 to 94.99 wt % of a volatile diluent to form a formulation; and
  applying the formulation onto the biological membrane, wherein said formulation cures in situ on the biological membrane to form the film.

2. The method according to claim 1 wherein the desired site comprises animal skin.

3. The method according to claim 1 wherein the film is less than 20 mils thick.

4. The method according to claim 1 wherein the desired site comprises flora.

5. A fast curing, film-forming formulation comprising:
  (A) 5–79.89 wt. % of an alkylene trialkoxy terminated polysiloxane;
  (B) 0–5 wt. % of an alkoxysilane;
  (C) 0.01–5 wt. % of a catalyst;
  (D) 0.1–25 wt % of a filler;
  (E) 20–94.89 wt % of a volatile diluent, wherein the total amount of (A) to (E) is 100 wt %; and
  (F) an active agent.

6. A fast curing, film-forming formulation comprising:
  (A) 5–79.99 wt. % of an alkylene trialkoxy terminated polysiloxane;
  (B) 0–5 wt. % of an alkoxysilane;
  (C) 0.01–5 wt. % of a catalyst;
  (D) 0.1–25 wt % of a filler;
  (E) 20–94.89 wt % of a volatile diluent, wherein the total amount nof (A) to (E) is 100 wt %; and
  (F) an ingredient selected from the group consisting of pH buffers, hydrophilic materials, modulating materials, swellable materials, and absorbant materials.

7. A fast curing, film-forming formulation comprising:
  (A) 5–79.99 wt. % of an alkylene trialkoxy terminated polysiloxane;
  (B) 0–5 wt. % of an alkoxysilane;
  (C) 0.01–5 wt. % of a catalyst;
  (D) 0.1–25 wt % of a filler;
  (E) 20–94.89 wt % of a volatile diluent, wherein the totaln amount of (A) to (E) is 100 wt %; and
  (F) an ingredient selected from the group consisting of water scavengers, colorants, colored indicators, excipients employed in pharmacy, stabilizers, preservatives, and surfactants.

8. The formulation according to claim 5 wherein the active agent is selected from the group consisting of cosmetics, antibiotics, antiseptics, antifungals, antibacterials, hormones, pain relief agents, anesthetics, anticancer agents, smoking cessation compositions, antiinflammatories, cardiovasculars, histamine blockers, bronchodilators, analgesics, antiarrythmics, alpha-1 blockers, beta blockers, ACE inhibitors, diuretics, antiaggregants, sedatives, tranquillisers, anticonvulsants, anticoagulants, vitamins, anti-aging agents, anticellulites, agents for treating gastric and duodenal ulcers, proteolytic enzymes, healing factors, peptides, pesticides, herbicides, UV protectors, perfumes, antiperspirants and deodorants, shaving products, absorbants, and pigments.

9. The formulation according to claim 5 wherein the active agent is present in the formulation at a concentration of from 0.1–70 parts by weight based on the weight of the formulation.

* * * * *